United States Patent [19]

Langrick

[11] Patent Number: 4,905,503

[45] Date of Patent: Mar. 6, 1990

[54] METHOD AND DEVICE FOR MEASURING THE VISCOSITY OF A FLUID

[75] Inventor: David J. Langrick, Lubenham, England

[73] Assignee: Willett International Limited, Chalvey, England

[21] Appl. No.: 311,615

[22] Filed: Feb. 15, 1989

Related U.S. Application Data

[63] Continuation-in-part of Ser. No. 224,730, Jul. 27, 1988, abandoned.

[30] Foreign Application Priority Data

Feb. 17, 1988 [GB] United Kingdom ................ 8803642

[51] Int. Cl.$^4$ ............................................ G01N 11/08
[52] U.S. Cl. ...................................................... 73/55
[58] Field of Search ...................................... 73/55, 56

[56] References Cited

U.S. PATENT DOCUMENTS

| | | | |
|---|---|---|---|
| 3,938,369 | 2/1976 | de Bok | 73/55 |
| 4,157,029 | 6/1979 | Leca et al. | 73/55 |
| 4,442,704 | 4/1984 | Swearingen | 73/55 |
| 4,644,781 | 2/1987 | Mon | 73/55 |
| 4,677,845 | 7/1987 | Izumi et al. | 73/56 |

FOREIGN PATENT DOCUMENTS 623051  8/1978  U.S.S.R. ................................. 73/55

*Primary Examiner*—Hezron E. Williams
*Assistant Examiner*—Joseph W. Roskos
*Attorney, Agent, or Firm*—Charles D. Gunter, Jr.

[57] ABSTRACT

A device for measuring the viscosity of a fluid is shown which can be used to continuously measure the viscosity of the ink used in an ink jet printer. The pressure between two restrictors which respond differently to a change in viscosity is related to the total pressure drop across both restrictors to provide an indication of the change in viscosity of the fluid being dispensed by the printer. By utilizing this information, the viscosity of the ink can be modified to maintain the viscosity within the desired range.

16 Claims, 2 Drawing Sheets

METHOD AND DEVICE FOR MEASURING THE VISCOSITY OF A FLUID

The present invention relates to a method and a device, and is a continuation-in-part of my co-pending application Ser. No. 07/224,730 filed July 27, 1988, now abandoned.

BACKGROUND TO THE INVENTION

In a continuous ink jet printer, ink is ejected continuously through a nozzle as a single jet of ink which is then broken up into a stream of substantially uniformly sized and spaced apart droplets, typically by applying pressure pulses to the ink or by vibrating the nozzle. The droplets are then caused to travel either into a collection gutter (in which case they are not printed) or are allowed to fall onto the surface on which the ink is to be applied. Typically, this is done by charging the droplets and then passing them through a deflecting electric field. The strength of the deflecting field and/or the charge on the droplets is varied to cause the line of flight of the droplets to be printed to depart to differing extents from the flight line to the gutter so that they miss the gutter and are printed at different positions on the substrate depending upon the extent to which they are deflected. Alternatively, the gutter is off set from the straight line of flight and the field deflects the droplets into the gutter at one extreme of the deflection. The term "ink jet printer" is used herein to denote the above type of printing apparatus.

The droplets which are collected in the gutter are not printed and are re-cycled to the ink reservoir serving the print head for re-use. However, during their flight and re-cycle, some of the solvent or carrier medium for the ink is lost from the droplets through evaporation.

The proper operation of the print head is dependent, inter alia, upon the viscosity of the ink flowing through the nozzle orifice and this is altered by the loss of solvent or carrier medium from the ink. The viscosity is also affected by the temperature at which the print head is operated and the composition of the ink, both of which latter can vary from print run to print run. It is therefore necessary to ensure that the viscosity of the ink is maintained within desired limits at all times and these limits may not be the same for each print run.

In practice it has proved difficult to maintain a uniform and consistent viscosity, since the losses of solvent or carrier medium are not consistent and vary considerably with the ambient conditions as well as with the relative proportion of droplets which are recycled to those which are printed.

It has been proposed to measure the weight lost from the ink in the reservoir of the ink jet printer; to allow for the proportion of that loss which is due to the ink in the droplets which have been printed; and then to add solvent or carrier medium to make up the apparent difference, assuming that this difference is made up totally by lost solvent or carrier medium. However, this is cumbersome and requires that the print head be shut down so that all ink in the system is returned to the reservoir for weighing. Furthermore, it does not take into account any extraneous losses or changes in temperature which can affect the viscosity of the ink.

In another method proposed in Japanese patent application No. 21723/1979, the rate of flow of ink is measured using a flow meter in a bypass line in the print head which is fed with ink under substantially constant pressure. Since the flow rate will vary with the viscosity, this gives an indication of the viscosity variations. However, if the pressure at which the ink is fed varies, this can mask any effect a viscosity change may have and accurate measurement and control of the feed pressure is required. Furthermore, flow meters require moving parts and do not give accurate readings at the comparatively low volume flow rates which are normal in ink jet printers.

It has also been proposed in European patent application No. 228828 to measure the time taken for ink to flow through a restricted inlet into a vessel and to fill that vessel between known lower and upper limits. However, such a system can only be operated if the pressure at which the ink is fed top the vessel is substantially constant. The system can anly be operated intermittently and requires extra controls for the operation of the filling and emptying of the vessel and the timing of the filling cycle.

It has also been proposed in European Application No. 0123523 to measure the pressure drop along a duct in the ink circuit when a valve in that duct is opened, the pressure drop being proportional to the viscosity of the ink in the duct. Again, that method cannot be operated continuously and requires control systems for the valve and requires a constant and/or accurately known volume flow of fluid to the duct, which is difficult to achieve in practice.

U.S. Pat. No. 3,938,369 describes a system in which the pressure drop along a capillary tube is measured at a constant volume flow rate through the tube. The pressure drop will vary with a change in the viscosity of the fluid, but this can only be monitored if the flow of fluid is held constant as required in this system. If the flow is allowed to vary, then the pressure drop due to that variation may mask any variation due to viscosity.

We have now devised a simple method for monitoring the change in viscosity of fluid flowing through a duct using a simple device which requires no moving parts. The method of the invention is not dependent upon maintaining a constant and/or accurately known pressure or volume flow rate through the duct, as has been required with the prior proposals. The viscosity can be monitored over a wide range of conditions with a simple device on a continuous basis and can be used to control the addition of solvent or carrier medium to the ink in an ink jet printer to optimise operation of the printer.

SUMMARY OF THE INVENTION

Accordingly, the present invention provides a method for monitoring the viscosity of a fluid, for example one flowing through a duct, which method is characterised in that:

a. the fluid is passed through a device comprising two non-identical flow restrictors connected in series, in which device the variation in the flow of fluid through one of the restrictors under the conditions of operation of the device with respect to a change in viscosity of the fluid is different to the variation of flow through the other restrictor for the same change in viscosity of the fluid flowing therethrough; and b. the pressure in the fluid between the restrictors relative to the pressure drop across the device is monitored to give an indication of a change in the viscosity of the fluid flowing through the device.

Preferably, the restrictors are connected in series by an intermediate conduit which imposes substantially no restriction on the flow of the fluid; and the pressure between the restrictors is measured in the fluid flowing through that conduit.

The invention measures the pressure between the restrictors (the intermediate pressure) and relates this to the pressure drop over the device. The operation of the device is automatic and does not rely upon the use of a constant or accurately known volume flow rate and can accommodate changes in the pressure at which the fluid is fed to and from the device. Thus, the invention can be applied to situations where the pressure drop across the device is substantially constant or where one of the inlet or outlet pressures in known, as when ink is fed by a constant pressure pump to the device, in which case changes in the viscosity of the fluid will be reflected in changes in the intermediate pressure.

In the case where the inlet and/or outlet pressures to and from the device vary, these will affect the flow rate of fluid through the device in a manner which can be predicted from the design and operating characteristics of the device. This effect may oppose, complement or even cancel out the effect on the flow rate through the device of a change in viscosity. However, the net effect on the intermediate pressure due to the change in viscosity can be readily calculated from the inlet and outlet pressures and their effect on the intermediate pressure. Thus, by measuring the inlet, intermediate and outlet pressures, the method of the invention provides a means for detecting changes in the viscosity of the fluid flowing through the device over a wide range of conditions, without the need for control over flow rates or the pressures as hitherto.

It is therefore preferred that in the method of the invention either the pressure drop across the device be maintained substantially constant, or the inlet and outlet pressures be monitored, for example by pressure sensors adjacent the inlet and outlet to the device.

The invention further provides a device for use in the method of the invention characterised in that it comprises two non-identical flow restrictors in series, preferably connected by a conduit, wherein:

a. the flow restrictors are selected such that under the intended conditions of use the flow rate of fluid through a first one of the said restrictors is affected more by a given change in the viscosity of the fluid than is the flow rate through the other restrictor for the same change in viscosity;

b. means are provided for monitoring the pressure in the fluid between the restrictOrs, for example in the conduit, and, optionally, the pressure drop across the device; and c. means are provided !Or relating the pressure in the between the restrictors to the pressure drop across the device and for providing an indication of a change in the viscosity of fluid flowing through the duct.

Preferably, the device comprises the two flow restrictors connected by a conduit with a pressure sensor adapted to measure the pressure of the fluid within the conduit, one or more pressure sensors being provided at the fluid inlet and/or the fluid outlet to the device to monitor the pressure drop across the device.

The invention finds especial use in monitoring changes of viscosity in a fluid flowing through a duct, and it is therefore preferred that the device is adapted to be mounted in fluid flow communication with a duct through which the fluid whose viscosity to be monitored is to flow.

The invention yet further provides an ink jet printer provided with a device of the invention adapted to monitor the viscosity of ink flowing through the printer and to cause addition of solvent and/or carrier medium to the ink so as to maintain the viscosity of the ink within desired limits.

The restrictors for present use can be selected from a wide range, for example needle valves, vortex restrictors, knife edge orifice plates, open cell foams, conduits with baffle plates or maze flow paths for the fluid, venturis and simple restricted bore or orifice tubes or plates. However, a particularly simple and preferred form of restrictor is a narrow bore tube or a plate having a wide bore aperture therethrough.

As stated above, the restrictors are selected so that the flow rate through them varies differently with respect to changes in viscosity. This can be achieved by the use of two similar types of restrictor having different dimensions. However, it is preferred to use two different types of restrictor, e.g. a needle valve for one restrictor and a venturi for the other. It is particularly preferred that one restrictor is a tube having a narrow bore therethrough and the other is a plate having a wide aperture therethrough.

Whilst the intermediate pressure will show a variation with restrictors which react to only a slightly different extent to changes in viscosity, it preferred to use restrictors which exhibit a difference of at least 10% in the variation in flow rate for a given change in viscosity, so that the variation in intermediate pressure can be readily detected using conventional pressure sensors.

Thus, with the preferred forms of restrictor, the narrow bore tube has a ratio of the bore length (1) to the bore diameter (d) greater than 5:1 so that the rate of flow through the bore at a given inlet pressure is primarily determined by the viscosity of the fluid. Ideally, the ratio l:d has a value greater than 10:1, e.g. of from 25:1 to 100:1; and the value of d is in the range 0.1 to 2 mms. Typically, the bore is provided by a length of stainless steel, glass or other capillary tube. Other forms of this restrictor include a long length of conventional tubing having a l:d ratio of 40:1 or more, e.g. 50:1 or more.

The other preferred restrictor is in the form of a comparatively large axial bore through a thin plate in which the ratio of the bore length (L) to the bore diameter (D) will be less than 5:1, preferably in the range 0.5:1 to 4:1. A typical other restrictor is a stainless steel or similar plate having an axial bore therethrough, the values of D being in the range 0.1 to 2 mms and L being from 0.1 to 1 mms. Alternatively, the other restrictor can be in the form of a drilled jewel orifice, as is typically used as the ink nozzle outlet in an ink jet printer.

It is preferred that the second restrictor in the series exerts a back pressure upon the first restrictor to achieve a readily detectable intermediate pressure in the conduit connecting the two restrictors. Typically, the back pressure will be in the range 0.5 to 5 bar and the optimum form of restrictor and its dimensions required to achieve the desired back pressure can readily be determined from theoretical considerations or by simple trial and error tests.

The two forms of restrictor are connected in series in either flow order. It may be feasible to connect the two restrictors directly to one another and to measure the intermediate pressure at the junction between them. However, it will usually be preferred to connect them by means of a conduit, so that there is an area between the two restrictors in which the intermediate pressure can be measured. For convenience, the invention will be described hereinafter in terms of the use of a conduit between the restrictors.

The conduit is one whose flow characteristics are substantially un-affected by changes in viscosity and preferably is one which imposes a minimal flow restriction between the two restrictors. The conduit can be of any suitable form, for example a comparatively wide bore tube or the like connecting the outlet from the first restrictor with the inlet to the second restrictor. In a preferred embodiment, the conduit comprises a hollow chamber having the restrictors mounted as the inlet and outlet to the chamber through the walls thereof. Preferably, the restrictors are located so that the effect of any dynamic pressure generated at the inlet to the chamber on the other restrictor is minimised. Thus, one restrictor can be located in an end wall of the chamber and the other in a side wall.

The pressure variations in the fluid within the conduit are measured by any suitable pressure sensing means. The optimum pressure sensing means for any given use can be selected from amongst those commercially available having suitable operating characteristics. Preferred pressure sensors for present use are those which give an electrical signal output which varies with the pressure observed However, sensors which give a mechanical, optical or other form of output may be used if desired. Preferably, the means is a transducer, notably a diaphragm type pressure transducer, mounted at any suitable point in the chamber, for example through the side wall of the chamber approximately equidistant between the two restrictors. Typically, for an ink jet printer, the pressure within the conduit will be in the range 0.5 to 5 bar and will vary by ±2 bar about the operating mean value.

As indicated above, the variation of the pressure within the conduit is related to the pressure drop across the device. This pressure drop can be predetermined and fixed by the design of the apparatus in which the device is to be used. However, it is preferred to monitor the inlet and/or the outlet pressure at the device so as to monitor any changes in the pressure drop across the device. Typically, in an ink jet printer, the ink will be fed at a substantially constant pressure to the print head from a reservoir by a pump; and the ink reservoir will usually be held at atmospheric pressure. The device of the invention can be located in a duct feeding ink from the output side of the pump to the reservoir, so that the pressure drop across the device will be substantially constant. Thus, it will usually be necessary to mount a pressure sensor only at the inlet to the device to monitor any changes in the inlet pressure. If desired, the outlet pressure can also be monitored, although this will usually not be necessary where the outlet from the device discharges to ambient pressure.

The signals from the pressure sensing means will indicate any change in pressure within the conduit and hence any change in the viscosity of the fluid flowing through the two restrictors. This signal can be fed to a suitable monitoring means which processes that signal into a form suitable for controlling the addition of solvent or carrier medium to the liquid flowing through the apparatus served by the device of the invention, e.g. to the reservoir for the re-cycled ink. Usually, the signal from the conduit sensor has to be related to the signals from the inlet and/or outlet sensors and integrated with respect to the design characteristics of each restrictor and of the device as a whole so that the pressure variations within the conduit are related to the change in viscosity of the fluid. The relationships used will depend upon the individual restrictor and conduit designs used in any given case and the relationship can be established using conventional hydrodynamic calculation techniques. The processing of the signals and their comparison with one another can be carried out using conventional electronic circuitry and techniques.

The method and device of the invention can be used to monitor the viscosity of a wide range of fluids. However, the invention is of especial use in monitoring the viscosity of ink compositions in an ink jet printer where the need for accurate control of the viscosity is of major importance and no satisfactory system exists. For convenience, the invention will be described hereinafter in terms of the monitoring of ink viscosity in an ink jet printer.

The viscosity of the ink can be adjusted in response to each signal output from the device of the invention, typically by the addition of solvent or carrier medium to make up for medium which has been lost from the ink by evaporation. However, this may require excessively rapid additions of very small amounts of solvent or carrier medium to compensate for minor variations in viscosity. It may therefore be preferred to monitor a series of signals and to actuate addition of solvent or carrier medium in response to the average of that series; or to monitor the change in the pressure difference between the conduit and the inlet or feed pressure and to make additions of given aliquots of solvent or carrier medium from a reservoir when the difference exceeds a given amount.

The viscosity of the fluid flowing in the duct will also be affected by temperature and it may be desired to incorporate some form of temperature sensing and compensation circuitry into the method and device of the invention using conventional techniques and equipment, for example during the processing of the signals from the pressure sensor means.

The device of the invention can be mounted at any suitable point in the fluid flow circuit to be monitored. Thus, in an ink jet printer, it can be mounted in the high pressure feed line between the pump and the print head or in the excess ink return line from the pump to the ink reservoir.

The device is operated by causing ink or other fluid to flow through the two restrictors and monitoring the variations in pressure within the conduit connecting them in relation to the pressure drop across the device. The variations in pressure are used to actuate the addition of solvent or carrier fluid to maintain the desired composition and viscosity and/or to actuate heaters to raise or lower the temperature of a hot melt ink so as to maintain the desired viscosity.

DESCRIPTION OF THE DRAWINGS

A preferred form of the invention will now be described by way of illustration with respect to the accompanying drawings in which.

DESCRIPTION OF PREFERRED EMBODIMENT

Figure 1:
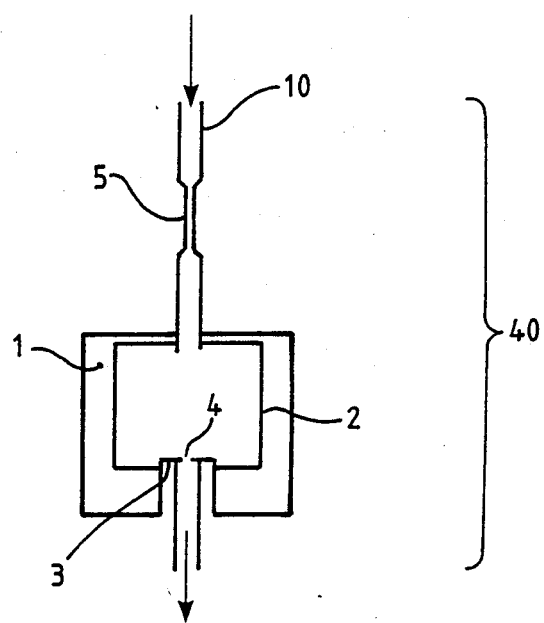
FIG. 1 is a diagrammatic side sectional view of the device.

The device comprises a plastics housing 1 having a diaphragm type pressure transducer 2 mounted radially through a side wall thereof at approximately the mid point of the housing. At the outlet end of the housing is jewel orifice 3 having a central axial bore 4 approximately 0.17 mms diameter forming one flow restrictor having a bore length to diameter ratio of approximately 2:1. The rate of flow of fluid through the restrictor is affected predominantly by the pressure drop across the jewel and only to a small extent by the viscosity of the ink.

At the other, inlet end of the housing is a capillary inlet tube 5 having an internal bore approximately 0.25 mms diameter and a length of approximately 25 mms providing the second restrictor for the device. The flow rate through this second restrictor is primarily dependent upon the viscosity of the fluid flowing through it. The inlet or outlet can be in a side wall of the housing rather than in the end walls as shown.

The device can be mounted so that fluid flows through it in the reverse sense to that shown.

A second transducer 10 is provided, in this case at the inlet to the device, so that the pressure changes within the housing can be related to the operating pressure of the ink system. The signals from the transducers 2 and 10 are fed to a conventional electronic comparitor circuit (not shown) which monitors the difference in the signals and detects when the difference varies by more than a predetermined amount from a desired level.

Figure 2:
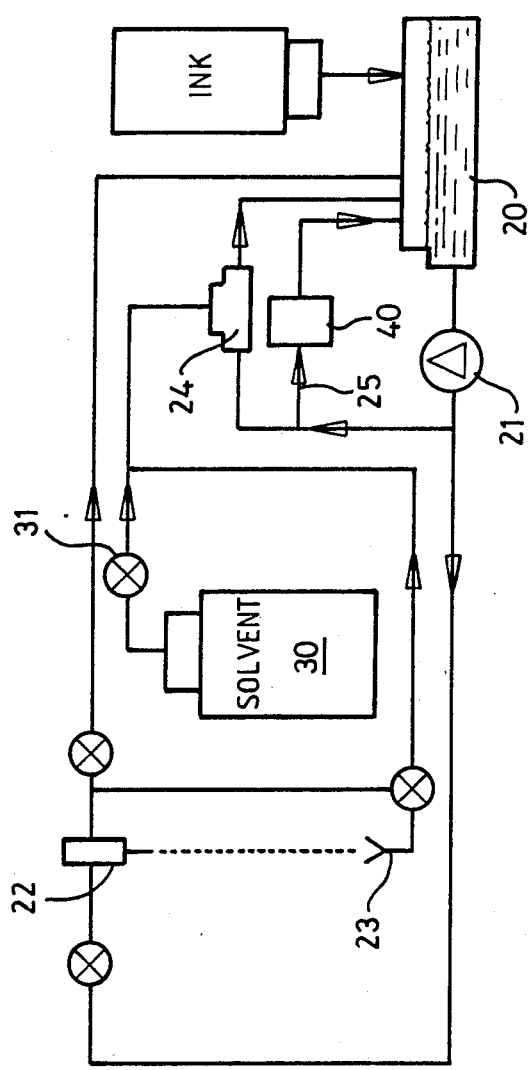
FIG. 2 is a diagrammatic block flow diagram of an ink jet printer incorporating the device of FIG. 1.

Typically, as shown in FIG. 2, the device will be located on a line from the pressure feed from the pump to the ink jet printing head so that the inlet pressure to the device is known and substantially constant. The outlet from the device feeds into the ink reservoir which is usually at substantially ambient pressure, so that the total pressure drop across the device is known, sensor 10 monitoring any changes in the inlet pressure which would affect the pressure drop.

In operation, ink is pumped around the ink jet printer from reservoir 20 by pump 21 at typically 2.5 to 4.5 bar to the printer nozzle 22 from which it issues as a single stream which is broken up into uniformly sized and spaced apart droplets. These are either printed or are caught in the gutter 23. The collected droplets are drawn by means of a venturi pump 24 from the gutter and returned to reservoir 20. Excess ink from pump 21 is returned to reservoir 20 by return line 25 in which is mounted device 40. Make-up solvent is held in reservoir 30 and fed to the ink reservoir 20 by the venturi pump when valve 31 is opened in response to signals from the device 40.

Initially, ink circulates through the ink jet printer and flows through the device 40. The pressure in housing 1 reaches an equilibrium value when the flow through the two restrictors is balanced at the substantially constant pressure in return line 25. This will give an equilibrium signal from the comparitor unit monitoring the output from transducers 2 and 10. If the viscosity of the ink changes, this will cause a change in the pressure within housing 1 and hence the signal output from transducer 2 changes and the difference between the signals from transducers 2 and 10 will rise or fall. When this difference deviates by more than a pre-set amount from that value corresponding to the desired viscosity for the fluid, valve 31 is caused to open to allow solvent to flow into reservoir 20 to adjust the composition of the ink and hence its viscosity.

By suitable conditioning of the electronic signals from the transducers 2 and 10, it is possible to minimise the effect of variations in the inlet pressure, allowing the difference signal to the comparitor to remain substantially invariant over a range of inlet pressures, typically 2 to 4 bar. Thus, a change in the operating pressure of the printer will not result in a false indication of a change in viscosity.

The above system has been modelled mathematically and the model confirms that the intermediate pressure in chamber 1 varies substantially linearly with the viscosity of the ink over an inlet pressure range of from 1.5 to 4.5 bar and a viscosity range of from 1 to 5 cps. The model also shows that, where the two restrictors are identical, the intermediate pressure in the chamber 1 is merely the mean of the inlet and outlet pressures and that it does not vary with changes in the viscosity of the ink.

The invention can be used to control the viscosity of fluids for a wide range of other purposes, for example to actuate a heater to control the viscosity of fuel oil when the temperature around the fuel line falls. The invention can also be used to achieve specific variations in viscosity of the fluid as opposed to maintaining the viscosity within a required range. Thus, the invention can be used to control the composition and viscosity of a fluid for individual stages of a multi-stage chemical process.

I claim:

1. A method for monitoring the viscosity of a fluid, which method comprises the steps of:
  a. passing the fluid through a device comprising two different characteristic flow restrictors connected in series, in which device the variation in the flow of fluid through one of the restrictors under the conditions of operation of the device with respect to a change in viscosity of the fluid differs by a detectable amount from the variation of flow through the other restrictor for the same change in viscosity of the fluid flowing therethrough; and
  b. monitoring the pressure in the fluid between the restrictors relative to the pressure drop across the device to give an indication of a change in the viscosity of the fluid flowing through the device.

2. A method as claimed in claim 1 wherein at least one of the inlet and outlet pressures to and from the device vary and at least one of those pressures is measured to monitor the pressure drop across the device.

3. A method as claimed in claim 1, wherein one restrictor comprises a narrow bore in which the ratio of the bore length to the bore diameter is greater than 5:1; and in that the other restrictor is provided by an axial bore having a length to diameter ratio of from 0.1:1 to less than 5:1.

4. A method as claimed in claim 1, wherein the restrictors are connected by a conduit.

5. A method as claimed in claim 1, wherein the fluid is an ink composition flowing through a duct of an ink jet printer apparatus and the viscosity of the ink is monitored to control the addition of carrier or solvent medium to the ink to maintain the viscosity thereof within predetermined limits.

6. A method for monitoring the viscosity of a fluid, which method comprises the steps of:
  a. passing the fluid through a device comprising two different characteristic flow restrictors connected in series, in which device the variation in the flow of fluid through one of the restrictors under the conditions of operation of the device with respect to a change in viscosity of the fluid differs by a detectable amount from the variation of flow through the other restrictor for the same change in viscosity of the fluid flowing therethrough;

b. monitoring the pressure in the fluid between the restrictors relative to the pressure drop across the device to give an indication of a change in the viscosity of the fluid flowing through the device; and wherein the method further comprises feeding fluid under pressure to the inlet of a first restrictor which is connected by a flow conduit chamber to the inlet of a second flow restrictor, the flow restrictors serving as the inlet and outlet to the chamber; measuring the pressure of the fluid within the chamber by means of a first pressure sensor; monitoring at least one of the inlet and outlet pressure of the fluid fed to and fed from the chamber by a second pressure sensor to provide an indication of the pressure drop across the chamber; by relating the pressure within the chamber to the pressure drop across the chamber, obtaining an indication of any changes in viscosity in the fluid flowing through the chamber; and utilising that indication to modify the viscosity of the fluid so as to maintain the viscosity within a desired range.

7. A method as claimed in claim 6, wherein the inlet pressure to the inlet to the chamber is substantially constant and the outlet to the chamber discharges to ambient pressure.

8. A device for monitoring the viscosity of a fluid, comprising:
   a. two different character flow restrictors connected in series, the flow restrictors being selected such that under the intended conditions of use the flow rate of fluid through a first one of the said restrictors is affected more by a given change in the viscosity of the fluid than is the flow rate through the other restrictor for the same change in viscosity;
   b. means provided for monitoring the pressure in the fluid between the restrictors; and
   c. means provided for relating the pressure between the restrictors to the pressure drop across the device and for providing an indication of a change in the viscosity of fluid flowing through the duct.

9. A device as claimed in claim 8 wherein the first restrictor is one having a narrow bore therethrough in which the ratio of the bore length (l) to the bore diameter (d) is greater than 5:1.

10. A device as claimed in claim 9, wherein the ratio l:d has a value of from 10:1 to 100:1 and the value of d is in the range 0.1 to 2 mms.

11. A device as claimed in claim 8, wherein the said other restrictor is one having a bore therethrough with a bore length to bore diameter ratio of between 0.1:1 to 5:1.

12. The device of claim 8, wherein the device is incorporated into an ink jet printer of the type having ink fed from a reservoir to a printing head, the device being adapted to monitor the viscosity of ink flowing through the printer and to cause addition of solvent and/or carrier medium to the ink so as to maintain the viscosity of the ink within a desired range of values.

13. A device as claimed in claim 8, wherein means are provided for monitoring the pressure drop across the device.

14. A device for monitoring the viscosity of a fluid, comprising:
   a. two different character flow restrictors connected in series, the flow restrictors being selected such that under the intended conditions of use the flow rate of fluid through a first one of the said restrictors is affected more by a given change in the viscosity of the fluid than is the flow rate through the other restrictor for the same change in viscosity;
   b. means provided for monitoring the pressure in the fluid between the restrictors;
   c. means provided for relating the pressure between the restrictors to the pressure drop across the device and for providing an indication of a change in the viscosity of fluid flowing through the duct; and
   wherein the device comprises a hollow chamber having one of said restrictors as the fluid inlet thereto and the other of said restrictor as the fluid outlet thereto.

15. A device as claimed in claim 14, wherein the chamber is provided with a sensor for measuring the pressure within the chamber and another sensor is provided at or adjacent the inlet to the device to measure the inlet pressure to the device.

16. An ink jet printer comprising:
   a. a reservoir for ink, a pump for delivering ink under pressure via a pressurised ink line to at least one ink jet nozzle for printing or for collection in a gutter for recycling to the reservoir;
   b. a device in a duct connected between the pressurized ink line and the reservoir, which device comprises a chamber through which the ink is to flow, said chamber having as an ink inlet thereto a first flow restrictor and as an ink outlet thereto a second flow restrictor, and the flow rate through the said first restrictor being affected to a different extent than the flow rate through the said second flow restrictor with respect to a change in viscosity in the ink;
   c. means comprising a pressure sensor to measure the pressure within the chamber, and optionally, at least one other pressure sensor to monitor at least one of the inlet and outlet pressures to the chamber to provide an indication of the pressure drop across the said device, said sensors producing output signals in accordance with the pressure observed by the sensor, and means for relating the signal from the said first sensor to the pressure drop across the device so as to produce an output signal from the device indicating a change in the viscosity of the fluid flowing through the chamber; and
   d. means responsive to the output signal from the device for feeding a solvent or carrier medium to the reservoir to maintain the viscosity of the ink within a desired range of values.

* * * * *